(12) United States Patent
Yu

(10) Patent No.: US 8,349,822 B2
(45) Date of Patent: Jan. 8, 2013

(54) TREATMENT OF CANCER WITH BIO AND CHEMOTHERAPY

(75) Inventor: John S. Yu, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 484 days.

(21) Appl. No.: 12/528,606

(22) PCT Filed: Feb. 25, 2008

(86) PCT No.: PCT/US2008/054918
§ 371 (c)(1),
(2), (4) Date: Aug. 25, 2009

(87) PCT Pub. No.: WO2008/106408
PCT Pub. Date: Sep. 4, 2008

(65) Prior Publication Data
US 2010/0068303 A1  Mar. 18, 2010

Related U.S. Application Data

(60) Provisional application No. 60/891,798, filed on Feb. 27, 2007.

(51) Int. Cl.
| | | |
|---|---|---|
| *A01N 43/00* | (2006.01) | |
| *A01N 43/42* | (2006.01) | |
| *A01N 43/38* | (2006.01) | |
| *A61K 31/33* | (2006.01) | |
| *A61K 31/44* | (2006.01) | |
| *A61K 31/405* | (2006.01) | |
| *C07C 259/00* | (2006.01) | |

(52) U.S. Cl. ......... 514/183; 514/283; 514/415; 564/253
(58) Field of Classification Search .................. 514/183, 514/283, 415; 564/253
See application file for complete search history.

(56) References Cited

FOREIGN PATENT DOCUMENTS
WO    2005041954 A1    10/2004

OTHER PUBLICATIONS

Beachy et al. Nature, 2004, vol. 432, pp. 324-331.*
PCT/US2008/054918 Written Opinion dated Jul. 3, 2008.
PCT/US2008/054918 IPRP dated Sep. 1, 2009.
Meijer et al. GSK-3-selective Inhibitors Derived from Tyrian Purple Indirubins. Chem Bio. (2003). 10(12):1255-1266.
Sato et al. Maintenance of Pluripotency in Human and Mouse Embryonic Stem Cells through Activation of Wnt Signaling by a Pharmacological GSK-3-specific Inhibitor. Nat Med. (2004). 10(1):55-63.

* cited by examiner

*Primary Examiner* — Samira Jean-Louis
(74) *Attorney, Agent, or Firm* — Linda B. Huber; Nixon Peabody LLP

(57) ABSTRACT

This invention relates to compositions and methods utilizing a chemotherapeutic drug and 6-bromoindirubin3'-oxime (BIO) for the treatment of cancer, including glioblastoma multiforme. The present invention demonstrates that BIO works synergistically with chemotherapeutic drugs to increase the cytotoxic effects of these drugs in glioma cells.

7 Claims, 13 Drawing Sheets

A  B

C  D

A

B

C

D

A 1  2  3  4  5  6  7  8  9  10  11  12  13

B 1  2  3  4  5  6  7  8  9  10  11  12  13

A 1  2  3  4  5  6  7  8  9

B 1  2  3  4  5  6  7  8  9

A

B

C

D

A

B

TREATMENT OF CANCER WITH BIO AND CHEMOTHERAPY

This application is the National Phase of International Application PCT/US08/54918, filed Feb. 25, 2008, which designated the U.S. and that International Application was published under PCT Article 21(2) in English. This application also includes a claim of priority under 35 U.S.C. §119(e) to U.S. provisional patent application No. 60/881,798, filed Feb. 27, 2007.

FIELD OF INVENTION

This invention relates to compositions and methods for the treatment of cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer remains among the leading causes of death in the United States and around the world. Various forms of cancer are differentially treated, depending in part on the location of a tumor. One particularly difficult group of tumors to treat includes those that reside in and near the brain. Treatment of brain tumors presents a number of problems, not the least of which being the dangers inherent in any surgical procedure involving regions of the brain and the tissue located nearby. There is little room for error and the consequences of even a minor surgical mishap can be devastating to a patient; brain damage, or even death may result. Still, where possible, surgery remains the preferred method of treatment for most brain tumors and is often performed in conjunction with radiation therapy and chemotherapy. However, even commonly referenced medical authority suggests that patients with brain tumors be referred to centers specializing in investigative therapies; an indication that conventional modes of treatment are not overwhelmingly successful.

Glioblastoma multiforme and anaplastic astrocytomas are classified in the category of brain tumors commonly known as malignant gliomas. Although not particularly common tumors themselves, they represent a class of tumors associated with significant rates of mortality and morbidity. Indeed, brain tumors are the third-most frequent cause of cancer-related death in middle-aged males and the leading cause of cancer death in children. According to the National Brain Tumor Foundation, approximately 190,000 people are diagnosed with primary or metastatic brain tumors in the United States each year. According to the Society for Neuroscience, approximately 20,000 cases of glioma are diagnosed each year, and more than half die within 18 months. For patients with the most severe, aggressive form of glioblastoma multiforme ("glioma" or "GBM"), median survival is less than a year. Current treatment for malignant glioma consists of surgical resection followed by radiation therapy and chemotherapy. However, this treatment generally fails in substantially changing the outcome for a patient. Thus, there remains a significant need in the art for improved methods for the treatment of cancer, and, in particular, for brain tumors.

Cancers are primarily comprised of a heterogeneous population of cells with marked differences in their proliferative potential. Cancer stem cells are a minor population of tumor cells that possess the stem cell property of self-renewal, and it is believed that dysregulation of stem cell self-renewal is a likely requirement for the development of cancer. (Al-Hajj, M. et al., *Therapeutic Implications of Cancer Stem Cells*, CURR. OPIN GENETIC DEV. 2004 14:43-47.)

Stem cells have the capacity to replicate themselves into cells with similar properties in order to maintain a pool of precursor cells. Adult stem cells, also called tissue stem cells, are found in differentiated tissues in which, in a controlled manner, they differentiate and/or divide to produce all the specialized cell types of the tissue from which they originate. Adult stem cells are often multipotent, capable to produce several but limited numbers of cell types. Normal tissue stem cells are typically defined by three common properties: (i) the presence of an extensive capacity for self-renewal that allows maintenance of the undifferentiated stem cell pool over the lifetime of the host; (ii) strict regulation of stem-cell number; and (iii) the ability to undergo a broad range of differentiation events to clonally reconstitute all of the functional elements within the tissue. Importantly, the stem cells in each tissue differ with respect to their intrinsic ability to both self-renew and to differentiate into particular mature cell types (Bixby, S. et al., *Cell-Intrinsic Differences Between Stem Cells From Different Regions Of The Peripheral Nervous System Regulate The Generation Of Neural Diversity*, NEURON 2002, 35:643-656).

The use of 6-bromoindirubin-3'-oxime ("BIO") to maintain embryonic stem cells in an undifferentiated state is known in the art. (Sato et al., *Maintenance of Pluripotency in Human and Mouse Embryonic Stem Cells through Activation of Wnt Signaling by a Pharmacological GSK-3-specific Inhibitor*, NAT. MED. (2004), 10(1), pp. 55-63, and Meijer et al., *GSK-3-selective Inhibitors Derived from Tyrian Purple Indirubins*, CHEM. BIOL. (2003), 10(12), pp. 1255-1266.) Indirubin-type compounds are also used to inhibit GSK-3 and other protein kinases. (International PCT Pat. App. Pub. No. WO 2005/041954, filed Oct. 28, 2004.) BIO has been isolated, included pharmaceutically acceptable compositions, salts, or vehicles thereof, and methods of inhibiting GSK-3 activity with BIO in vitro or in a cell have been described.

Several genes initially linked to carcinogenesis have been implicated in the regulation of the normal stem-cell self-renewal process, including the Bmi-1, Notch, Wnt and Sonic hedgehog pathways. (Spink, K. E. et al., *Structural Basis of the Axinadenomatous Polyposis Coli Interaction*, EMBO J. 2000, 19:2270-2279; Taipale, J. et al., *The Hedgehog and Wnt Signaling Pathways In Cancer*, NATURE 2001, 411:349-354; Bhardwaj, G. et al., *Sonic Hedgehog Induces the Proliferation of Primitive Human Hematopoietic Cells Via Bmp Regulation*, NAT IMMUNOL 2001, 2:172-180; Austin, T. W. et al., *A Role for the Wnt Gene Family In Hematopoiesis: Expansion of Multilineage Progenitor Cells*, BLOOD 1997, 89:3624-3635.) For example, Reya et al. (*A Role for Wnt Signaling in Self-Renewal of Hematopoietic Stem Cells*, NATURE 2003, 423:409-414) demonstrated the dependence of normal HSC self-renewal decisions on Wnt-signaling through the canonical pathway. Willert et al. demonstrated the ability of purified Wnt3a to permit the in vitro expansion of transplantable HSCs. (Willert, K. et al., *Wnt Proteins Are Lipid-Modified and Can Act as Stem Cell Growth Factors*, NATURE 2003, 423:448-452.) Additional studies implicate the Wnt/b-catenin pathway in the maintenance of stem-cell self-renewal in other tissues as well. (Andl, T. et al., *Wnt Signals Are Required for the Initiation of Hair Follicle Development*, DEV CELL 2002, 2:643-653; Jamora, C. et al., *Links Between Signal Transduction, Transcription and Adhesion in Epithelial Bud Development*, NATURE 2003, 422:317-322.)

Cyclins and cyclin-dependent kinases (CDK) are key regulators in mammalian cell cycle. Regulation of these complexes occurs through cyclin production and destruction, relocation, inhibitory and activating phosphorylation events, relocation and also via the effects of other proteins. Each cyclin associates with one or two CDKs and most CDKs associate with one or two cyclins. CDK1 forms a complex with cyclin A/B and regulates phosphorylation of cytoskeleton proteins involved in mitosis. CDK2 and CDK3 form complexes with cyclin E which regulate the G1-S phase transition while the CDK2/CycA complex regulates S phase progression. CDK4/CycD and CDK6/CycD are activated by mitogenic signaling during early G1 and progressively accumulate as cells transition through this phase of the cell cycle. CDK5 is activated in postmitotic neurons and regulates neuron migration during brain development. CDK7/CycH is believed to be a link between transcription and cell cycle. CDK8/CycC and CDK9/CycT are involved in transcription. The kinase activity of CDKs is tightly regulated by phosphorylation and protein-protein interactions. Activation of CDKs requires binding to a specific cyclin and phosphorylation of a conserved threonine residue in a region called the T loop. Examining the phosphorylation of peptides by CDK/cyclin complexes suggests that both CDKs and cyclins play a role in recognizing substrates. A consensus sequence, (S/T)PX(R/K), is identified in the peptides that are phosphorylated by CDK/cyclins.

Cyclin-dependent kinase activity is regulated by T-loop phosphorylation, by the abundance of their cyclin partners and by association with CDK inhibitors of the Cip/Kip or INK family of proteins. The inactive ternary complex of CDK4/cyclin D and p27 Kip1/Cip1 requires extracellular mitogenic stimuli for the release and degradation of p27, which affects progression through the restriction point and pRb-dependent entry into S-phase. The active complex of CDK4/cyclin D targets the retinoblastoma protein for phosphorylation, allowing the release of E2F transcription factors that activate G1/S-phase gene expression. In HeLa cells, upon UV irradiation, upregulation of p16 INK4a association with CDK4/cyclin D3 leads to a G2 delay, implicating CDK4/cyclinD3 activity in progression through G2-phase of the cell cycle.

SUMMARY OF THE INVENTION

Various embodiments of present invention provide for methods, compositions and kits that target pathways involved in malignant stem-cell self-renewal to increase the cytotoxic effects of chemotherapeutic agents and to treat cancer.

The present invention provides for a method for treating cancer in a subject in need thereof, comprising: providing a glycogen synthase kinase-3 ("GSK-3") antagonist and/or Wnt canonical pathway agonist and a chemotherapeutic drug; and administering the GSK-3 antagonist and/or Wnt canonical pathway agonist and the chemotherapeutic drug to the subject to treat the cancer.

In various embodiments the GSK-3 antagonist and/or Wnt canonical pathway agonist may be 6-bromoindirubin-3'-oxime ("BIO") or methylated BIO ("MeBIO"). The chemotherapeutic drug used in the method may be selected from the group consisting of temozolomide ("Tmz"), VP-16, paclitaxel, carboplatin, tumor necrosis factor-related apoptosis-inducing ligand ("TRAIL"), troglitazone ("TGZ"), pioglitazone ("PGZ"), rosiglitazone ("RGZ"), and ciglitazone ("CGZ"), procarbazine, vincristine, BCNU, CCNU, thalidomide, irinotecan, isotretinoin, imatinib, etoposide, cisplatin, daunorubicin, doxorubicin, methotrexate, mercaptopurine, fluorouracil, hydroxyurea, vinblastine and combinations thereof. One particularly useful chemotherapeutic drug may be Tmz. In a specific embodiment, the GSK-3 antagonist and/or Wnt canonical pathway agonist may be BIO or MeBIO and the chemotherapeutic drug may be Tmz. The administration of the chemotherapeutic agents and the GSK-3 antagonist and/or Wnt canonical pathway agonist may include, without limitation, delivery of the compounds together, delivery of each compound separately, delivery as a single dosage, delivery periodically, or delivery of the compounds separately and/or at different intervals.

In one embodiment the cancer treated may be brain cancer. Particular brain cancers that may be treated by the inventive method may include but are not limited to glioma, glioblastoma multiforme, astrocytoma, pituitary adenoma, acoustic neuroma, meningioma, oligodendrogliomas, gangliocytoma, ependymoma, medulloblastoma, medulloepithelioma, neuroblastoma, retinoblastoma, ependymoblastoma, pineocytoma, pineoblastoma, ependymal cell tumors, choroid plexus tumors, gliomatosis cerebri, and astroblastoma.

The present invention also provides a composition for the treatment of cancer, comprising: a glycogen synthase kinase-3 ("GSK-3") antagonist and/or Wnt canonical pathway agonist; a chemotherapeutic drug; and a pharmaceutically acceptable carrier. The GSK-3 antagonist and/or Wnt canonical pathway agonist may be BIO or MeBIO. Chemotherapeutic drugs used for the composition may include but are not limited to Tmz, VP-16, paclitaxel, carboplatin, TRAIL, TGZ, PGZ, RGZ, and CGZ, procarbazine, vincristine, BCNU, CCNU, thalidomide, irinotecan, isotretinoin, imatinib, etoposide, cisplatin, daunorubicin, doxorubicin, methotrexate, mercaptopurine, fluorouracil, hydroxyurea, vinblastine. One particularly useful chemotherapeutic agent may be Tmz. In one particular embodiment, the composition may comprise BIO or MeBIO and Tmz.

The present invention additionally provides for a method to increase cytotoxic effect of a chemotherapeutic drug in a subject in need thereof, comprising: providing a glycogen synthase kinase-3 ("GSK-3") antagonist and/or Wnt canonical pathway agonist; and administering the GSK-3 antagonist and/or Wnt canonical pathway agonist to the subject to increase the cytotoxic effect of the chemotherapeutic drug. The GSK-3 antagonist and/or Wnt canonical pathway agonist may be a compound as described above. The chemotherapeutic drug may also be a compound as described above. In one particular embodiment, the GSK-3 antagonist and/or Wnt canonical pathway agonist may be BIO or MeBIO and the chemotherapeutic drug may be Tmz.

The present invention further provides a kit for the treatment of cancer, comprising: a glycogen synthase kinase-3 ("GSK-3") antagonist and/or Wnt canonical pathway agonist as described above; a chemotherapeutic drug as described above; and instructions to use the GSK-3 antagonist and/or Wnt canonical pathway agonist and the chemotherapeutic drug to treat the cancer.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
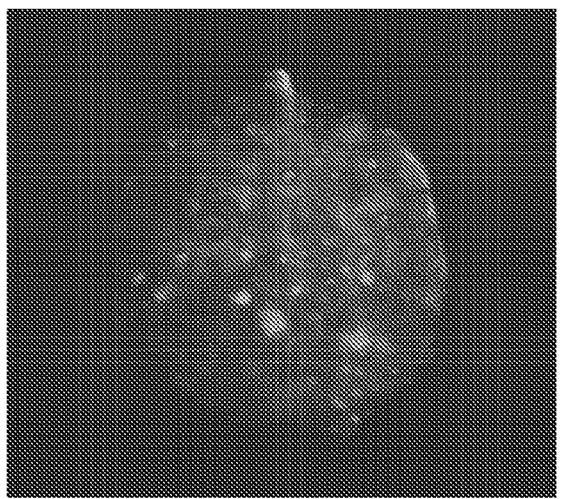
FIG. 1 depicts human GBM derived neurospheres stained with stem cell markers in accordance with various embodiments of the present invention. (A) CD133; (B) Nestin; (C) Nuclear counterstained with DAPI; (D) Merged A, B and C. Magnification is 200×.
Figure 1:
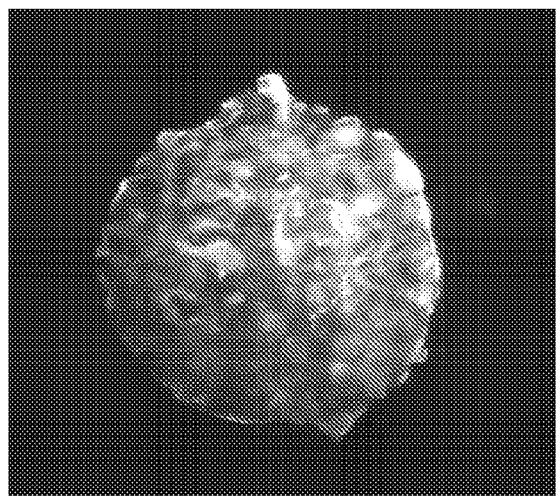
Figure 1:
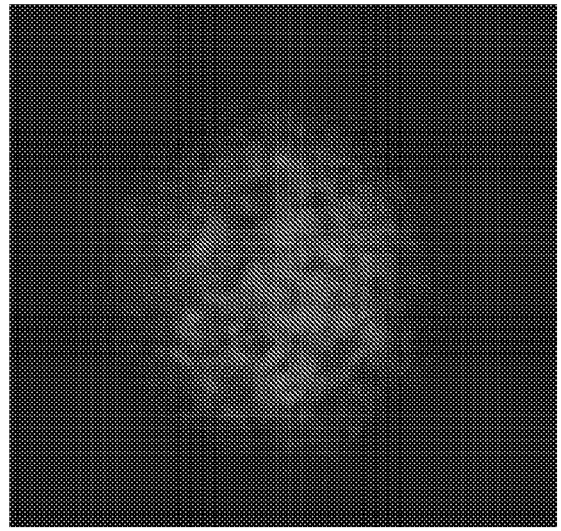
Figure 1:
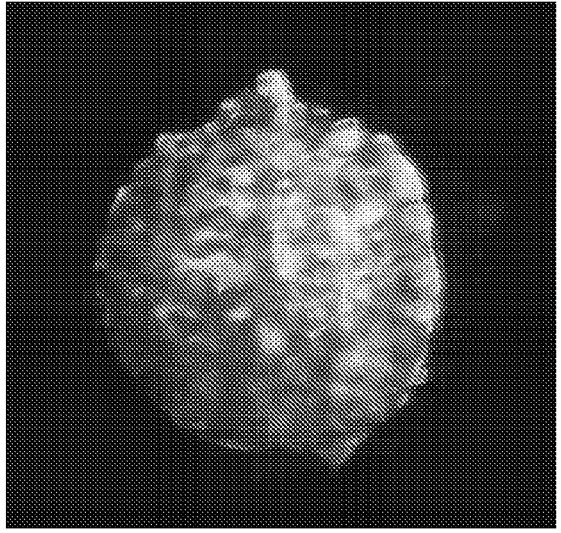

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Alleviating" specific cancers and/or their pathology includes degrading a tumor, for example, breaking down the structural integrity or connective tissue of a tumor, such that the tumor size is reduced when compared to the tumor size before treatment. "Alleviating" metastasis of cancer includes reducing the rate at which the cancer spreads to other organs.

"Beneficial results" may include, but are in no way limited to, preventing, reducing, preventing the increase of and inhibiting the pathology of cancer. Beneficial results may also refer to curing the cancer and prolonging a patient's life or life expectancy.

"Cancer" and "cancerous" refer to or describe the physiological condition in mammals that is typically characterized by unregulated cell growth. Examples of cancer include, but are not limited to, ovarian cancer, breast cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, head and neck cancer, and brain cancer; particularly, glioma, glioblastoma multiforme, astrocytoma, pituitary adenoma, acoustic neuroma, meningioma, oligodendrogliomas, gangliocytoma, ependymoma, medulloblastoma, medulloepithelioma, neuroblastoma, retinoblastoma, ependymoblastoma, pineocytoma, pineoblastoma, ependymal cell tumors, choroid plexus tumors, gliomatosis cerebri and astroblastoma.

"Cancer stem cell" is an operational term defined as a cancer cell that has the ability to self-renew giving rise to another malignant stem cell as well as undergo differentiation to give rise to phenotypically diverse nontumorigenic cancer cells. DNA and tissue microarrays of tumors to date have failed to account for the cellular heterogeneity as well as differences in the proliferative potential of these different populations. Thus, there is a need in the art for treatments that directly target those pathways involved in malignant stemcell self-renewal.

"Conditions" and "disease conditions," as used herein may include, but are in no way limited to any form of cancer; in particular, glioma, glioblastoma multiforme, astrocytoma, pituitary adenoma, acoustic neuroma, meningioma, oligodendrogliomas, gangliocytoma, ependymoma, medulloblastoma, medulloepithelioma, neuroblastoma, retinoblastoma, ependymoblastoma, pineocytoma, pineoblastoma, ependymal cell tumors, choroid plexus tumors, gliomatosis cerebri and astroblastoma.

"Curing" cancer includes degrading a tumor such that a tumor cannot be detected after treatment. The tumor may be reduced in size or become undetectable, for example, by atrophying from lack of blood supply or by being attacked or degraded by one or more components administered according to the invention.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Pathology" of cancer includes all phenomena that compromise the well-being of the patient. This includes, without limitation, resistance to cytotoxic agents (e.g., chemotherapeutic agents), abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Therapeutically effective amount" as used herein refers to that amount which is capable of achieving beneficial results in a patient with cancer. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, lower or reverse the pathology of cancer cells or tumors even if the treatment is ultimately unsuccessful. Those in need of treatment include those already with cancer as well as those prone to having cancer or those in whom the cancer is to be prevented.

"Tumor," as used herein refers to all neoplastic cell growth and proliferation, whether malignant or benign, and all precancerous and cancerous cells and tissues.

"Therapeutic agent" as used herein refers to agents with the capability to prevent, inhibit, reduce, stop and/or reverse the pathology of cancer cells or tumors.

The present invention is directed to compositions and methods for the treatment of cancer in patients. The inventor demonstrated in human cells that 6-bromoindirubin-3'-oxime (BIO) works in synergy with chemotherapeutic agents (e.g., temozolomide (Tmz), VP-16, Taxol, carboplatin) to enhance treatment of cancer, specifically gliomas. Additionally, BIO may reduce the toxic effect of some traditional cancer therapies. BIO is a GSK-3 (glycogen synthase kinase-3) antagonist, and induces the Wnt canonical pathway of cancer stem cell self-renewal. Irregular GSK-3 activity has been implicated in many human diseases, including cancer. BIO targets the self-renewal mechanism of the cancer stem cells of the particular cancer to initiate the self-renewal mechanism. This takes the stem cell out of quiescence and allows the chemotherapeutic agent to kill the dividing stem cell. Thus, the present invention provides for compositions and methods comprising the combination of a GSK-3 antagonist and/or an agonist of the Wnt canonical pathway of stem cell self renewal and a chemotherapeutic drug to treat cancer. Further, the use of BIO synergistically with a chemotherapeutic drug (e.g., Tmz, VP-16, Taxol) to increase the cytotoxic effect of the drug in glioma cells is contemplated by the present invention. Thus, BIO enhances the cytotoxic effect of anti-neoplastic agents, such as Tmz, VP16 and Taxol, by targeting cancer stem-cell self-renewal in cancer cells. Any number of chemotherapeutic drugs may be used. In one embodiment, the chemotherapeutic drug may affect DNA replication; for example, DNA alkylating agents.

In various embodiments, a treatment for disease conditions, such as cancer, includes compositions comprised of at least one chemotherapeutic agent and a glycogen synthase kinase-3 ("GSK-3") antagonist and/or Wnt canonical pathway agonist (e.g., BIO). The compositions of the present invention may be administered to a mammal to alleviate, and potentially cure, a host of disease conditions; particularly cancer, and more particularly, cancers of the brain, such as GBM.

The chemotherapeutic agents used in connection with the present invention may be selected from any chemotherapeutic agent, as will be readily appreciated by one of skill in the art. Chemotherapeutic agents are known to those of skill in the art and may be used, either alone or in combination with still further chemotherapeutic agents and BIO, in connection with alternate embodiments of the present invention. Many other chemotherapeutic agents will be readily recognized by those of skill in the art and can be used in connection with the present invention without undue experimentation. Examples of such chemotherapeutic agents may include, but are in no way limited to, tumor necrosis factor-related apoptosis-inducing ligand ("TRAIL"), troglitazone ("TGZ"), pioglitazone ("PGZ"), rosiglitazone ("RGZ"), and ciglitazone ("CGZ"), VP-16 and Taxol, temozolomide, procarbazine, carboplatin, vincristine, BCNU, CCNU, thalidomide, irinotecan, isotretinoin (available from Hoffman-LaRoche, Inc. under the tradename Accutane®), imatinib (available from Novartis Pharmaceuticals Corporation under the tradename Gleevec®), etoposide, cisplatin, daunorubicin, doxorubicin, methotrexate, mercaptopurine, fluorouracil, hydroxyurea, vinblastine and paclitaxel (Taxol®). It will also be readily appreciated by those of skill in the art that, while a single chemotherapeutic agent may be administered to treat cancer in connection with various embodiments of the present invention, a wide array of combinations of chemotherapeutic agents may alternatively be administered in the treatment of cancer. Moreover, chemotherapeutic agents may be administered by any suitable delivery route, such as, without limitation, oral (PO), intravenous (IV), intrathecal (IT), intraarterial, intracavitary, intramuscular (IM), intralesional or topical.

The chemotherapeutic agents and BIO used in connection with the present invention may be combined in a composition using any conventional technique, as will be readily appreciated by one of skill in the art. Alternatively, the administration of the chemotherapeutic agents and BIO of the invention may include, without limitation, delivery of the compounds together, delivery of each compound separately, delivery as a single dosage, delivery periodically, or delivery of the compounds separately and/or at different intervals, although other schemes of administration may be used, as will be readily appreciated by those skilled in the art. "Periodically," as used herein includes, but is in no way limited to, any interval of time such as hourly, daily, weekly, twice weekly, and monthly as would be recognized by one skilled in the art.

The quantity of the chemotherapeutic agents and BIO of the composition appropriate for administration to a patient as a cancer therapy to effect the methods of the present invention and the most convenient route of such administration may be based upon a variety of factors, as may the formulation of the composition itself. Some of these factors may include, but are in no way limited to, the physical characteristics of the patient (e.g., age, weight, sex, etc.), the physical characteristics of the tumor (e.g., location, size, rate of growth, accessibility, etc.), and the extent to which other therapeutic methodologies (including chemotherapy and radiation therapy) are being implemented in connection with an overall treatment regimen. Additional administrations may be effected, depending upon the above-described and other factors, such as the severity of tumor pathology.

Any conventional pharmaceutical carrier may be used with the compositions in accordance with the present invention, and an appropriate carrier may be selected by one of skill in the art by routine techniques. For example, one may formulate the pharmaceutical carrier of the composition differently in order to account for different delivery techniques for the composition, physiological differences among patients (e.g., sex, weight, age, etc.), or different types of tumors (e.g., brain, breast, lung, etc.), among other factors. The composition administered to a mammal in accordance with the present invention may be delivered in combination with any of a variety of additional substances and compounds; for example, any suitable carrier, vehicle, additive, excipient, pharmaceutical adjunct, or other suitable product. Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling may include amount, frequency, and method of administration.

The compositions may be administered to a mammal (e.g., a human) by any conventional technique in accordance with various embodiments of the present invention for the treatment of a disease condition, such as cancer and/or a tumor; in particular, brain cancer and/or a brain tumor. The compositions may be delivered in an amount sufficient to alleviate or cure the disease condition and/or to achieve beneficial results. The compositions may be administered by any conventional delivery route, either alone or in combination with other chemotherapeutic agents or cancer therapy (e.g., radiation therapy). The compositions may be administered by any appropriate technique, as will be readily appreciated by those of skill in the art. By way of example and not to be interpreted as limiting, the composition and/or therapy may be administered via oral administration or intravenous administration.

In other embodiments, a method for treating cancer or cancerous tumors in mammals is provided. The method comprises providing compositions capable of alleviating or curing the disease condition, and administering a therapeutically effective amount of the compositions to a cancer patient to treat the cancer. The method may include providing at least one chemotherapeutic agent and a glycogen synthase kinase-3 ("GSK-3") antagonist and/or Wnt canonical pathway agonist (e.g., BIO); and implementing a combination therapy to the recipient in a manner to treat the particular condition. Furthermore, the chemotherapeutic agents and BIO may have characteristics similar to the compositions described above in accordance with alternate embodiments.

There are various reasons why one might wish to administer a composition including both chemotherapeutic agents and BIO rather than administering these compounds separately in a combination therapy. Depending on the particular chemotherapeutic agents and BIO that one uses, a composition might have superior characteristics as far as clinical efficacy, solubility, absorption, stability, toxicity and/or patient acceptability are concerned. It will be readily apparent to one of ordinary skill in the art how one can formulate a composition of any of a number of combinations of chemotherapeutic agents and BIO. There are many strategies for doing so, any one of which may be implemented by routine experimentation. For example, the pharmacokinetics of the chemotherapeutic agents and BIO may determine the administration of the compounds.

The determination of a therapeutically effective dose is well within the capability of those skilled in the art. A "therapeutically effective" dose refers to that amount of active ingredient which increases or decreases the effects of a disease condition relative to that which occurs in the absence of the therapeutically effective dose. Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50. Furthermore, the data obtained from cell culture assays and animal studies is used in formulating a range of dosage for human use, which can be readily tended to by one of ordinary skill in the art without undue experimentation. The dosage contained in such compositions may be selected so as to be within a range of circulating concentrations that include the ED50 with little or no toxicity. The dosage varies within this range depending upon the dosage form employed, sensitivity of the patient, and the route of administration.

The appropriate dosage of the chemotherapeutic agents and BIO of the invention may depend on a variety of factors. Such factors may include, but are in no way limited to, a patient's physical characteristics (e.g., age, weight, sex), whether the compound is being used as single agent or adjuvant therapy, the type of condition being treated, the progression (i.e., pathological state) of the cancer, and other factors that may be recognized by one skilled in the art. Furthermore, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans. However, the exact dosage will be determined by the practitioner, in light of factors related to the subject that requires treatment.

In a further embodiment of the present invention, a kit is provided for the treatment of cancer in a mammal. In one embodiment, the kit may be configured for cancers of the brain; for instance, for the treatment of GBM. The kit is useful for practicing the inventive method of treating disease conditions. The kit is an assemblage of materials or components. Kits for treating disease conditions may include compositions comprising at least one chemotherapeutic agent and a glycogen synthase kinase-3 ("GSK-3") antagonist and/or Wnt canonical pathway agonist (e.g., BIO) capable of alleviating or curing the disease condition. Furthermore, the chemotherapeutic agents and BIO may have characteristics similar to the compositions described above in accordance with alternate embodiments.

The exact nature of the components configured in the inventive kit depends on its intended purpose. For example, some embodiments are configured for the purpose of treating the disease condition of patients with cancer. In one embodiment, the kit is specifically configured for the purpose of treating the disease condition of patients with brain cancer. In various embodiments, kits may be configured particularly for the purpose of treating mammalian subjects. In other embodiments, kits are configured for veterinary applications, diagnosing or treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to alleviate or cure a cancer patient's disease condition. Optionally, the kit also contains other useful components, such as diluents, buffers, pharmaceutically acceptable carriers, syringes, catheters, applicators, pipetting or measuring tools or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit. The packaging material is constructed by well known methods, preferably to provide a sterile, contaminant-free environment. The packaging materials employed in the kit are those customarily utilized in treating cancer. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Isolating and Culturing Brain Tumor Cells

Brain tumor cells may be isolated by methods known in the art. Cancer stem cells from brain tumors may be isolated as described in Yuan et al., *Isolation of Cancer Stem Cells from Adult Glioblastoma Multiforme*, ONCOGENE. 2004 Dec. 23(58):9394-9400.

A human primary cultured glioma (MG-328) was established from the surgical specimen of a patient with newly diagnosed glioblastoma at Cedars-Sinai Medical Center after Institutional Review Board-approved consent was obtained. MG-328 and human glioma cell lines, U-87MG (American Type Culture Collection, Manassas, Va.) and LN-18 (provided by Dr. Erwin Van Meier, Emory University, GA), were maintained at 37° C. and 5% $CO_2$ in Dulbecco's modified Eagle's medium/F-12 with 10% heat-inactivated fetal bovine serum, 2 mM glutamate, 10 mM HEPES, 100 units/ml penicillin, and 100 μg/ml streptomycin.

Example 2

Cellular Proliferation Assay

Figure 2:
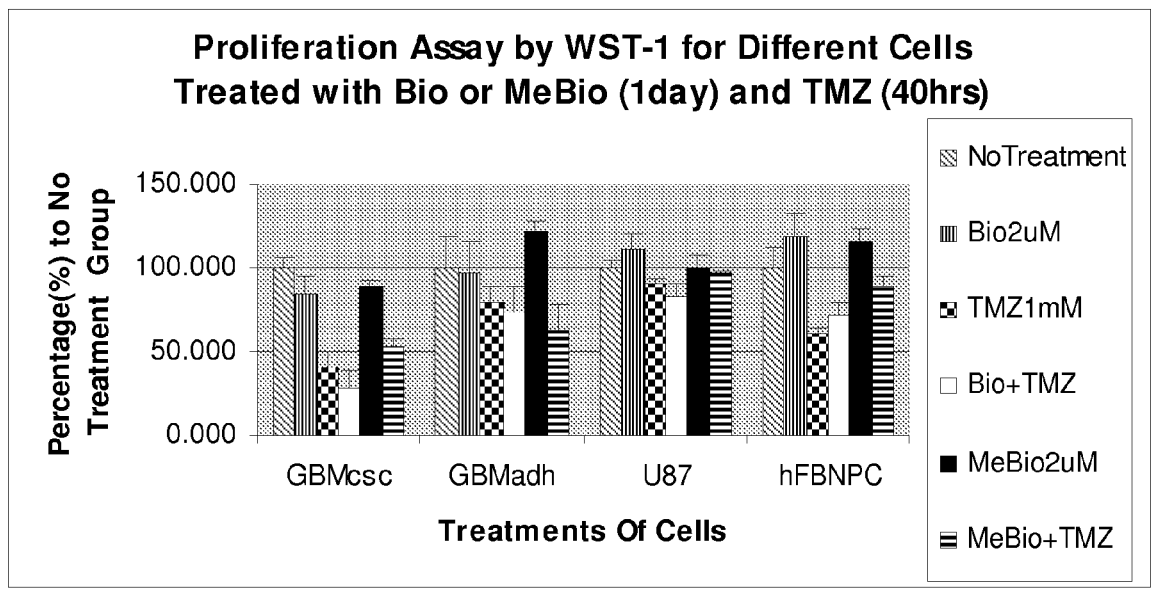
FIG. 2 depicts a proliferation assay by WST-1 for different cells treated with BIO or MeBIO and Tmz in accordance with an embodiment of the present invention.
Figure 3:
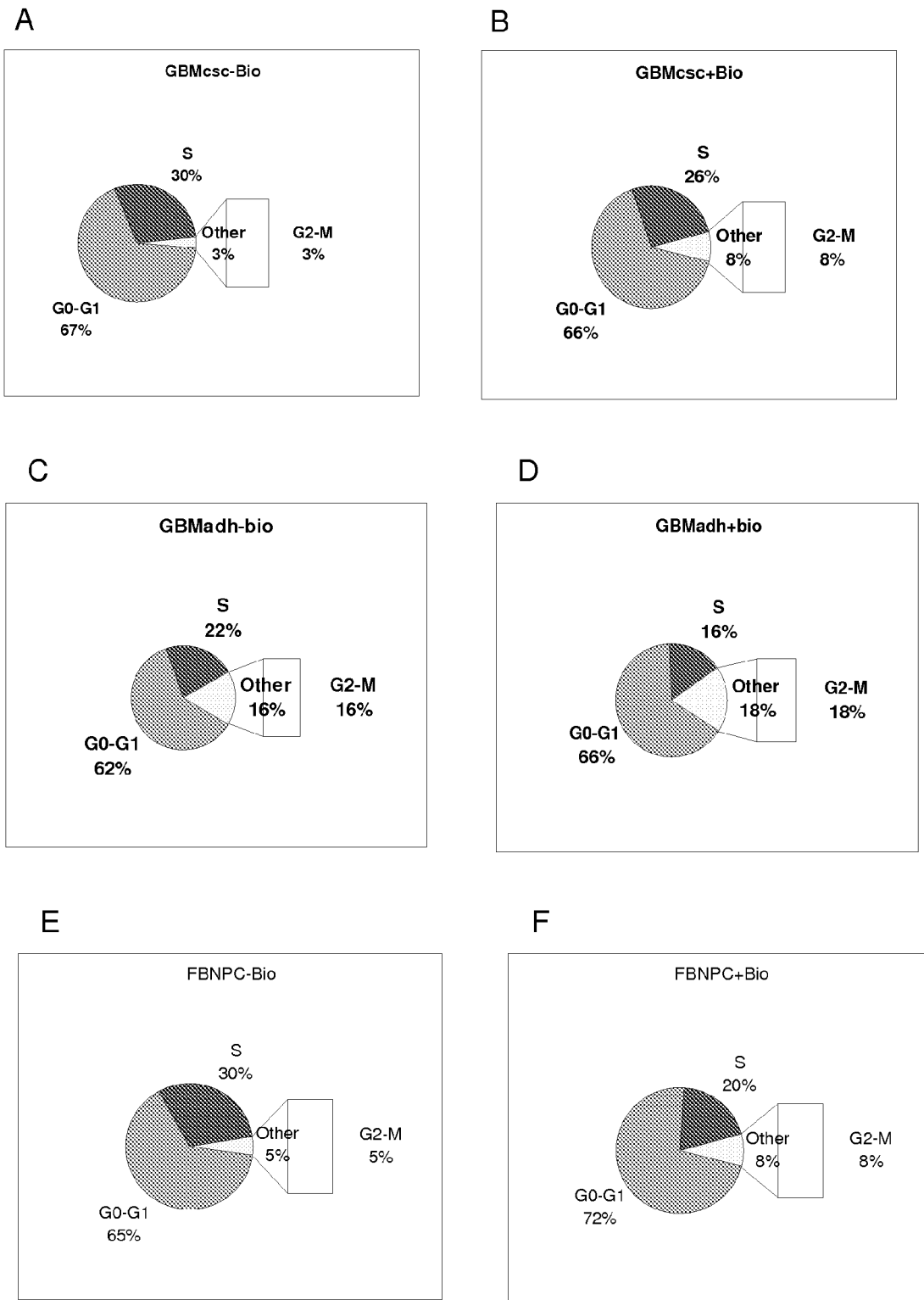
FIG. 3 depicts cell cycle analysis after BIO treatment in accordance with an embodiment of the present invention. (A) GBM CSC−BIO; (B): GBM CSC+BIO; (C) GBM Adh−BIO; (D) GBM Adh+BIO; (E): FBNPC−BIO; (F): FBNPC+BIO.

Proliferation assays by Wst-1 for different cells treated with BIO or MeBIO and Tmz were performed. The results are summarized and depicted in table 1 and FIG. 2.

TABLE 1

|  | GBM CSC | GBMAdh | U87 | hFBNPC |
|---|---|---|---|---|
| No Treatment | 100 ± 5.94 | 100 ± 18.89 | 100 ± 4.29 | 100 ± 12.46 |
| BIO 2 μM | 83.89 ± 11.30 | 97.21 ± 17.97 | 110.23 ± 10.15 | 118.00 ± 14.77 |
| Tmz 1 mM | 40.55 ± 9.48 | 79.15 ± 10.49 | 89.98 ± 4.21 | 60.34 ± 4.06 |
| BIO + Tmz | 28.35 ± 10.85 | 73.17 ± 15.37 | 82.76 ± 7.40 | 72.33 ± 7.46 |
| MeBIO | 88.70 ± 3.6 | 121.43 ± 6.09 | 99.83 ± 7.28 | 115.73 ± 8.21 |
| MeBIO + Tmz | 53.25 ± 4.38 | 62.13 ± 16.63 | 96.49 ± 2.28 | 88.80 ± 5.80 |

Example 3

Apoptosis Assay

Figure 4:
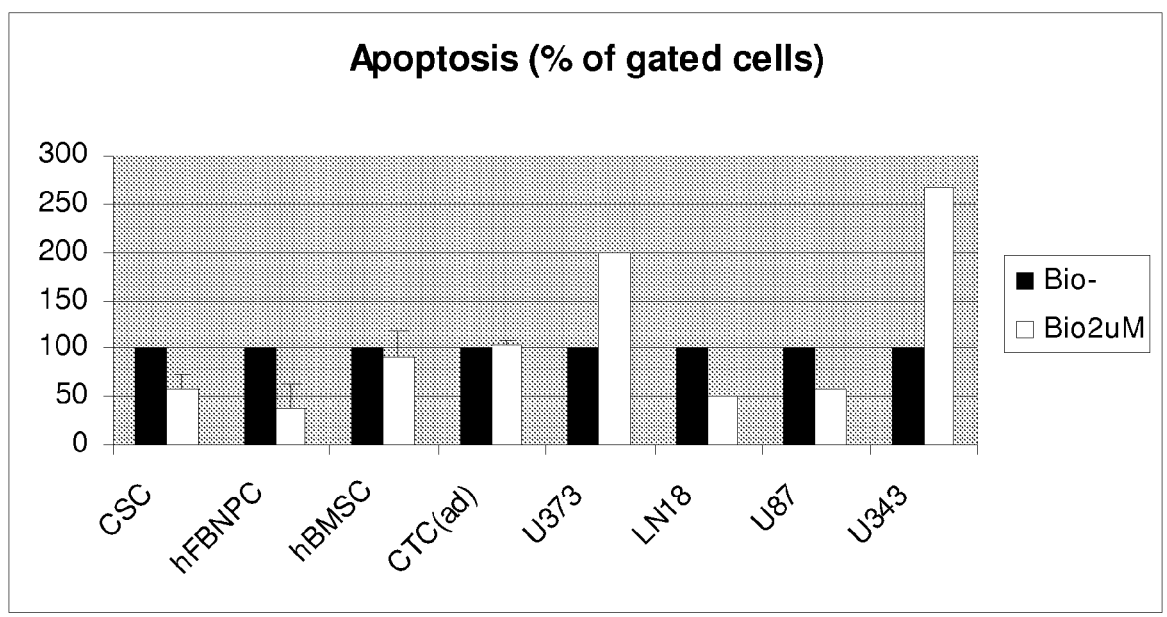
FIG. 4 depicts apoptosis of cells in accordance with an embodiment of the present invention.
Figure 5:
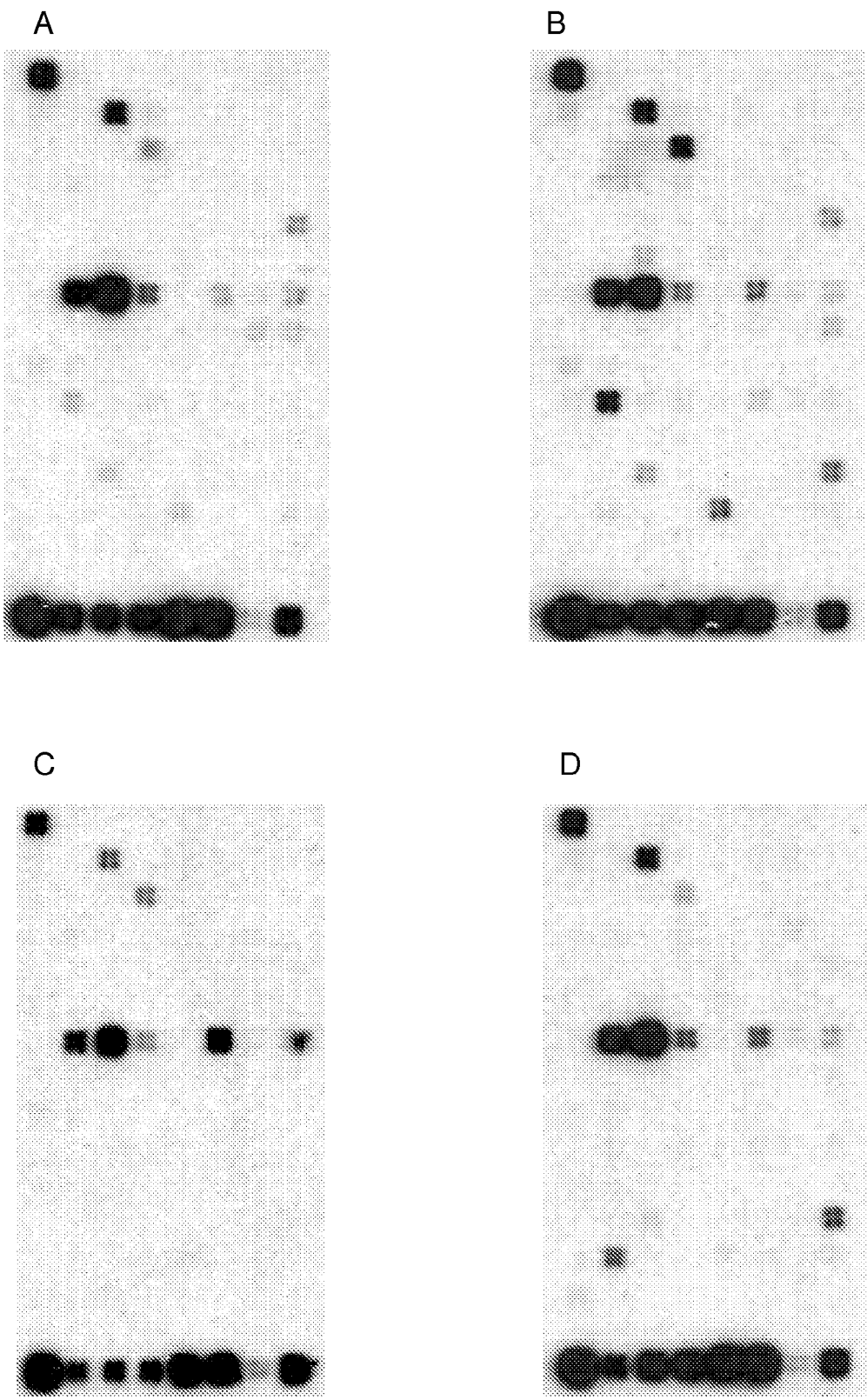
FIG. 5 depicts SuperArray Assays for BIO treated cancer cells and cancer stem cells in accordance with an embodiment of the present invention. (A) DA CSC−BIO; (B) DA CSC+BIO; (C) DA Adh−BIO; (D) DA Adh+BIO.
Figure 6:
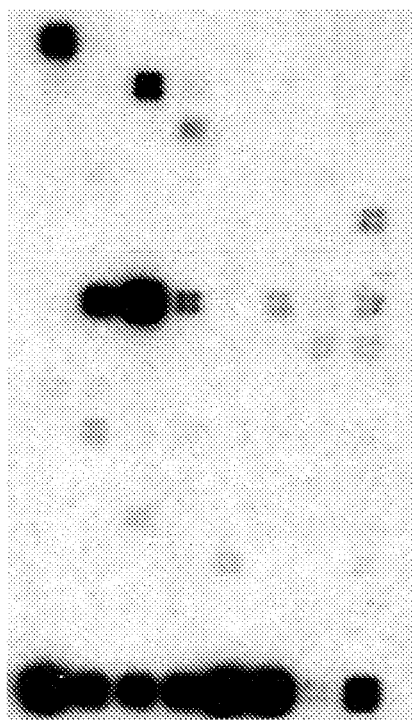
FIG. 6 depicts SuperArray Assays for BIO treated stem cells and hFBNPCs in accordance with an embodiment of the present invention. (A) DA CSC−BIO; (B) DA CSC+BIO; (C) hFBNPC−BIO; (D) hFBNPC+BIO.
Figure 6:
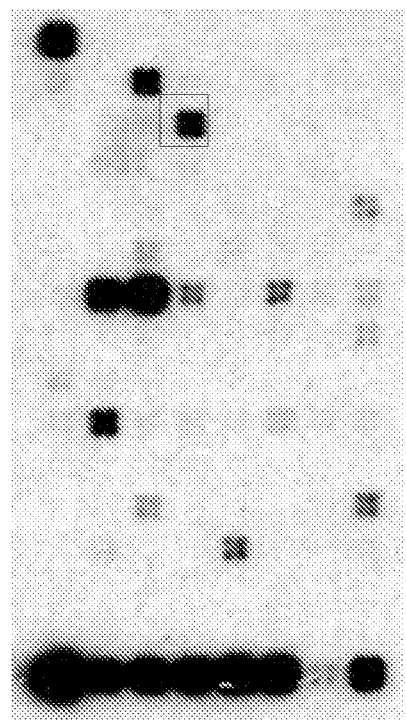
Figure 6:
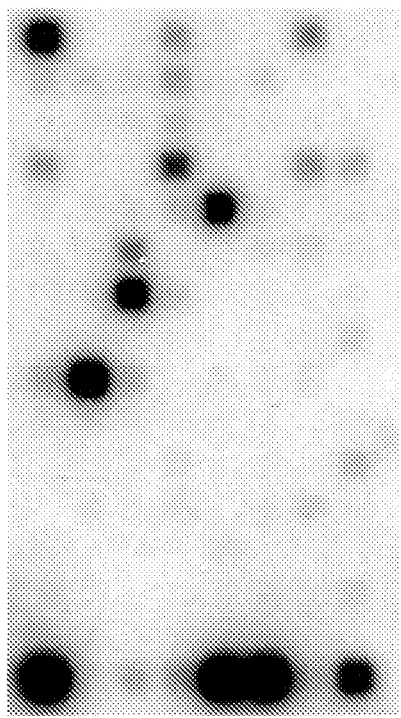
Figure 6:
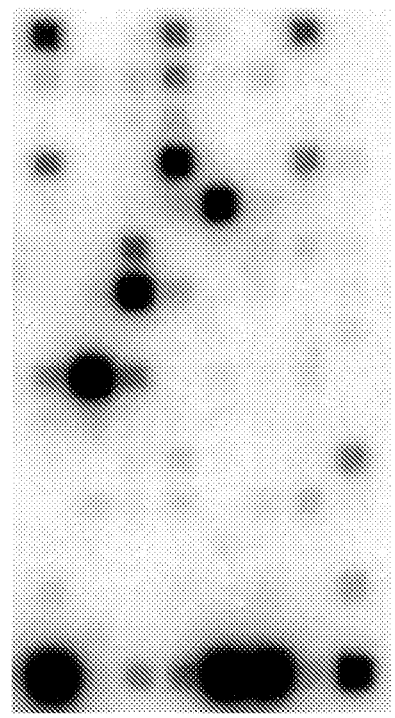
Figure 7:
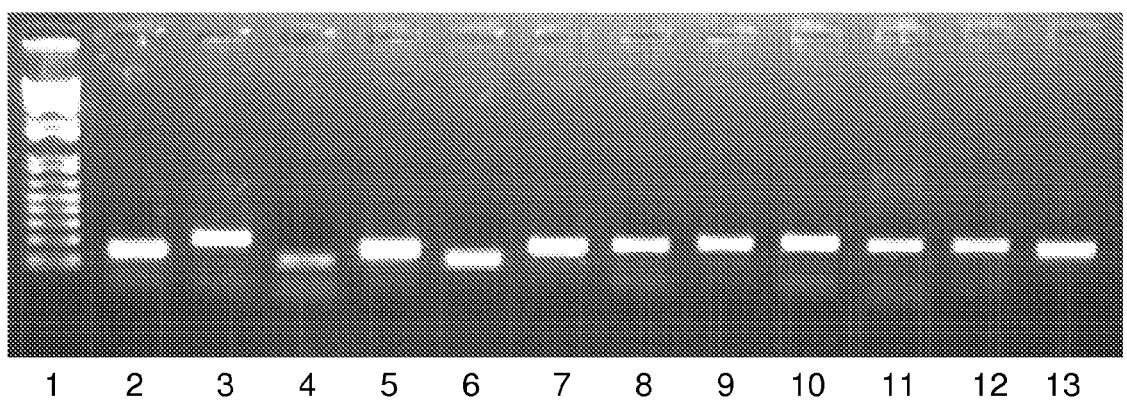
FIG. 7 depicts CDKs expression in CSC and hFBNPC in accordance with an embodiment of the present invention. (A) GBM7 CSC; (B) hFBNPC. Lanes: (1) DNA ladder; (2) CDC2; (3) CDK2; (4) CDK3; (5) CDK4; (6) CDK5; (7) CDK6; (8) CDK7; (9) CDK8; (10) CDK9; (11) CDK10, (12) CDK11; (13) GAPDH.
Figure 7:
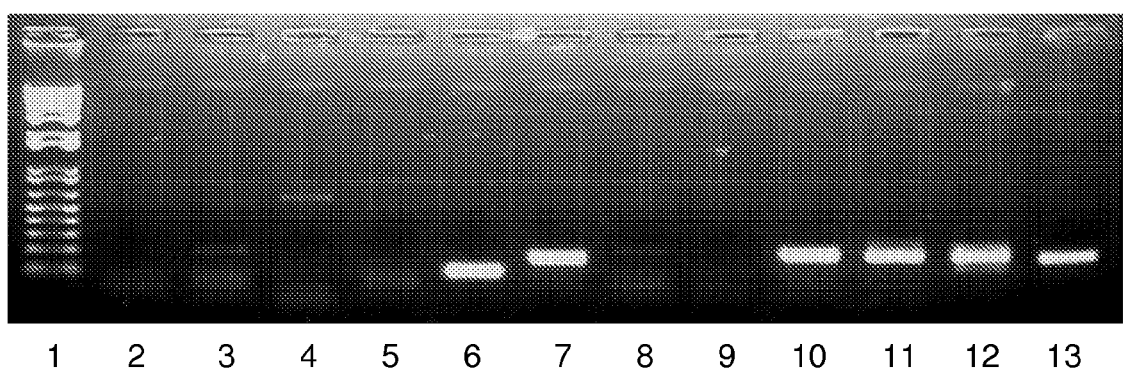
Figure 8:
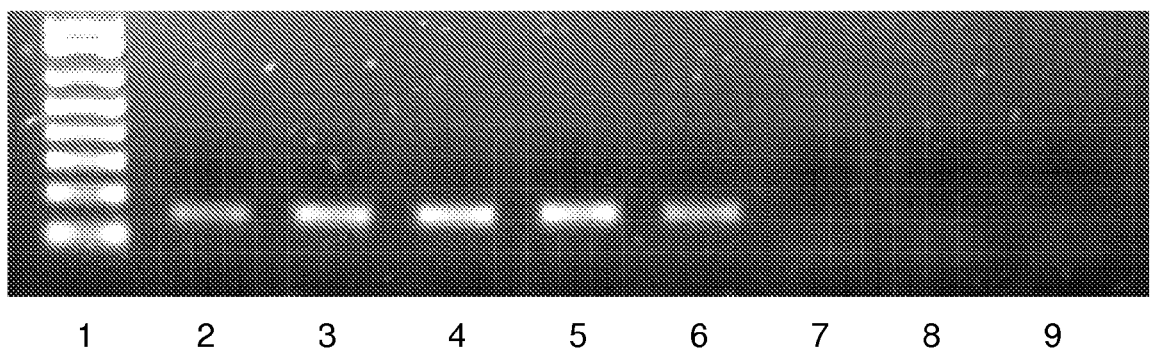
FIG. 8 depicts CCNE expression in different cells in accordance with an embodiment of the present invention. (A) CCNE; (B) GAPDH. Lanes: (1) DNA ladder; (2) GBM7 CSC; (3) GBM7 Adh; (4) GBM17 CSC NT; (5) GBM17 CSC BIO; (6) GBM17 CSC MeBIO; (7) hFBNPC NT; (8) hFBNPC BIO; (9) hFBNPC MeBIO.
Figure 8:
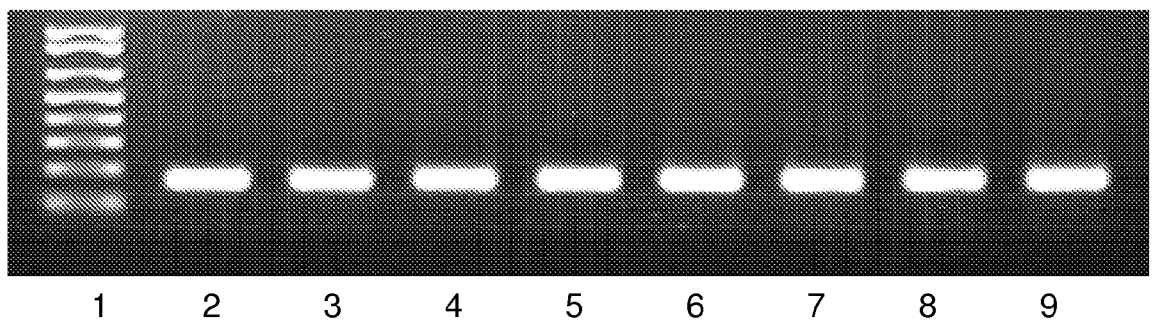
Figure 9:
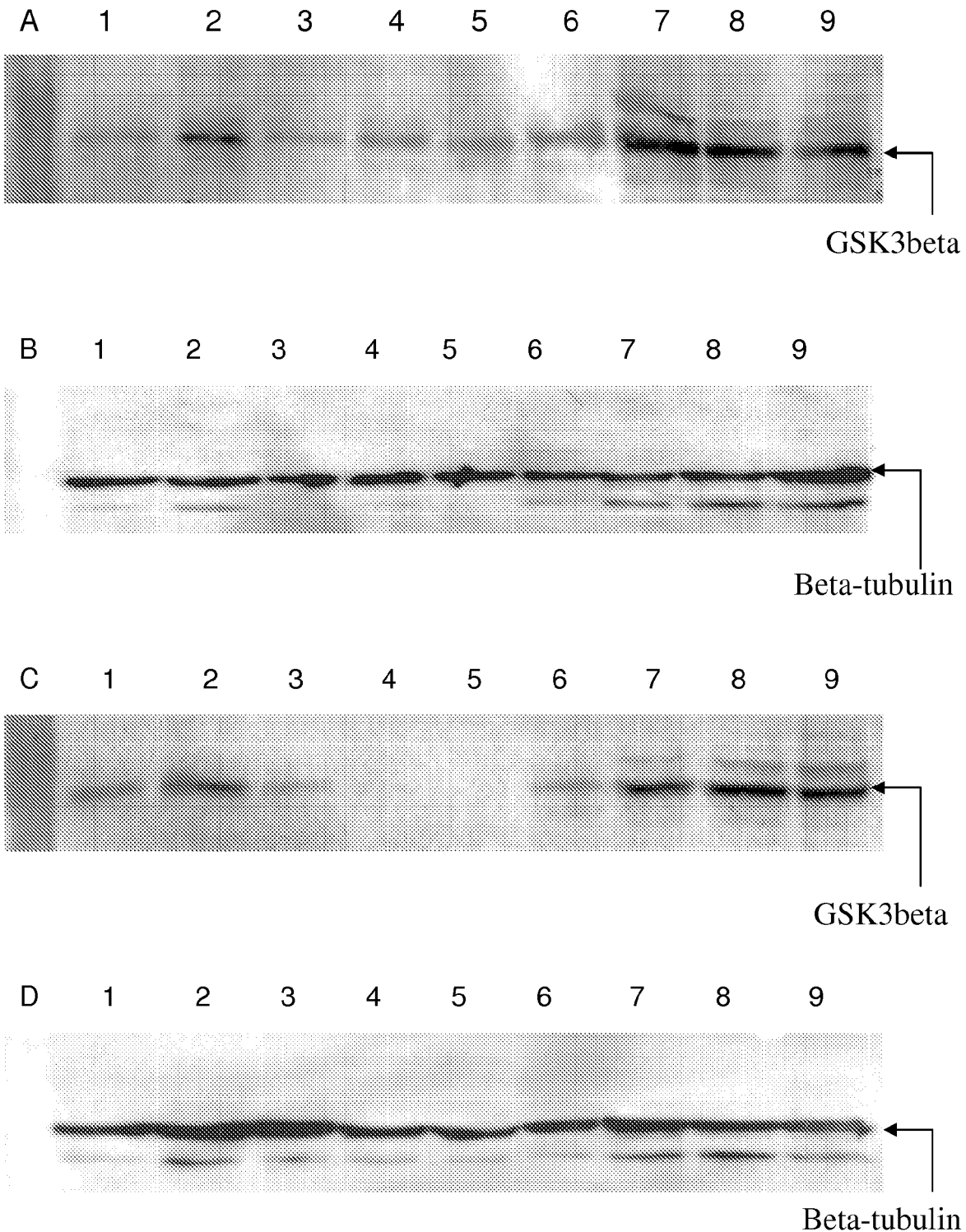
FIG. 9 depicts the presence or absence of GSK3beta and Beta-tubulin in GBM7 CSC and GBM12 CSC in accordance with various embodiments of the present invention. (A) GBM7 CSC detecting GSK3 beta; (B) GBM7 CSC detecting Beta-tubulin; (C) GBM12 CSC detecting GSK3 beta; (D) GBM12 CSC detecting Beta-tubulin. Lanes: (1) CSC with no treatment (NT); (2) CSC treated with BIO; (3) CSC treated with MeBIO; (4) Adherent cells with NT; (5) Adherent cells treated with BIO; (6) Adherent cells treated with MeBIO; (7) hFBNPC with NT; (8) hFBNPC treated with BIO; (9) hFBNPC treated with MeBIO.
Figure 10:
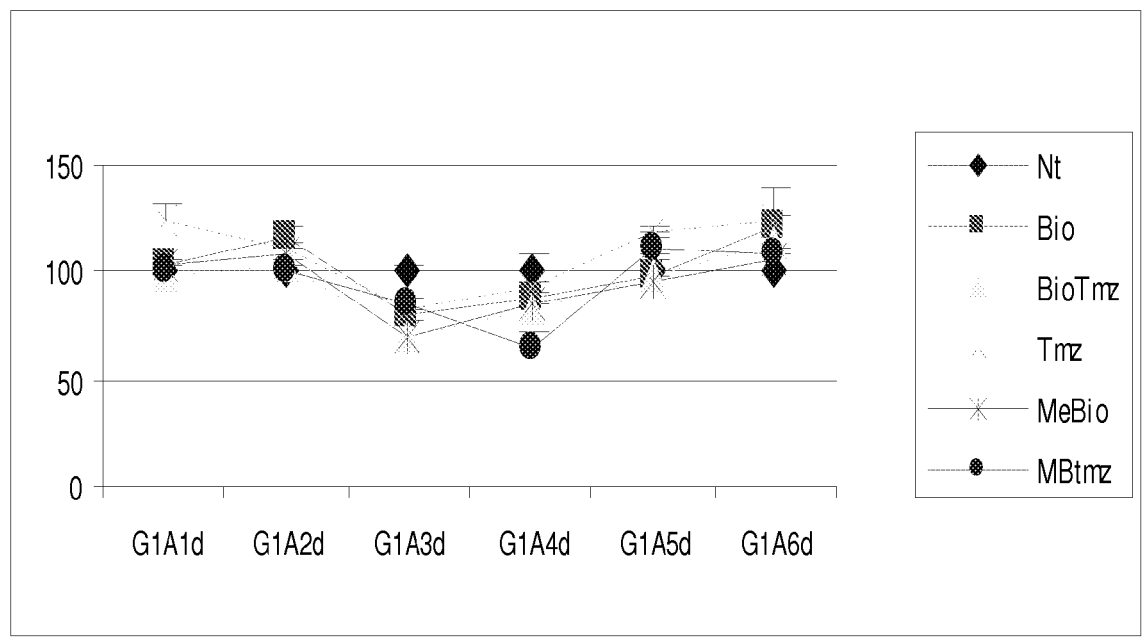
FIG. 10 depicts the time course of cells treated with BIO, BIO+Tmz, Tmz, MeBIO, MeBIO+Tmz, or no treatment in accordance with various embodiments of the present invention. The cells were treated for different days and Tmz was added for 40 hours.
Figure 10:
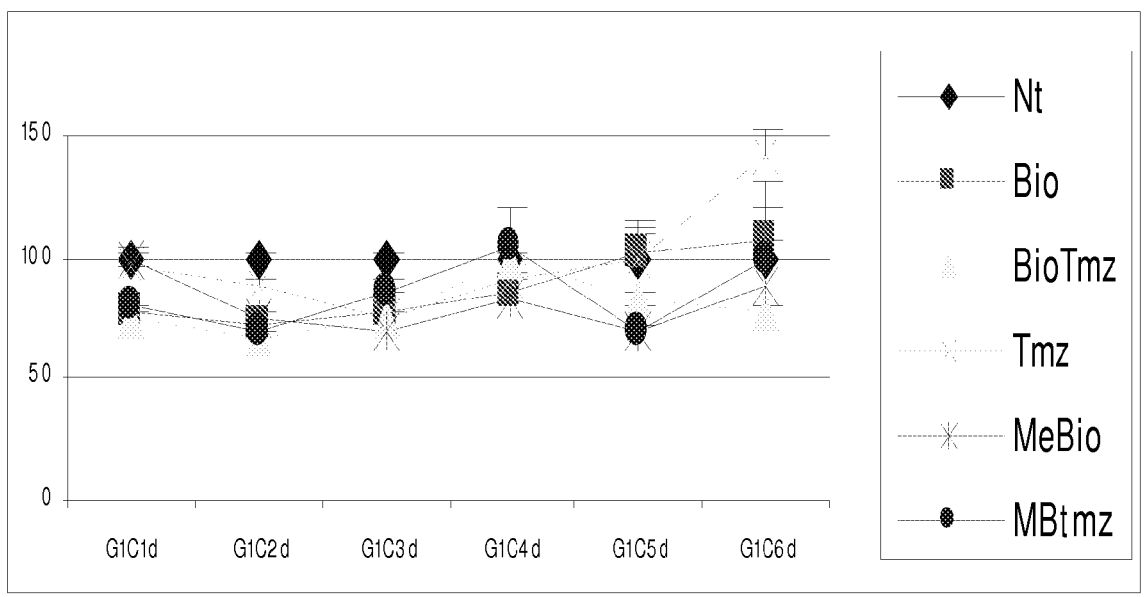
Figure 10:
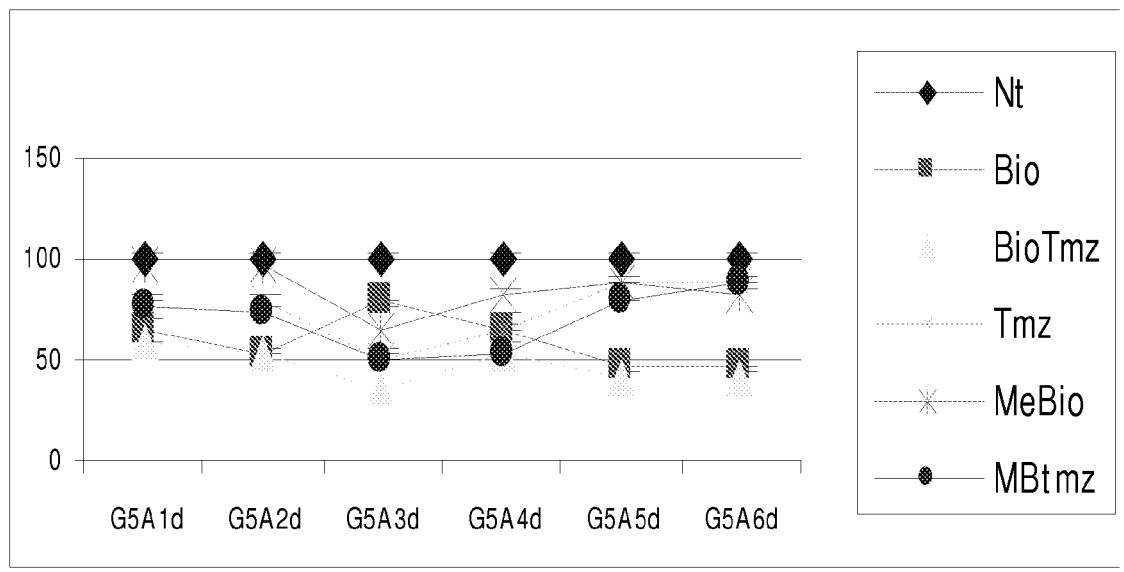
Figure 10:
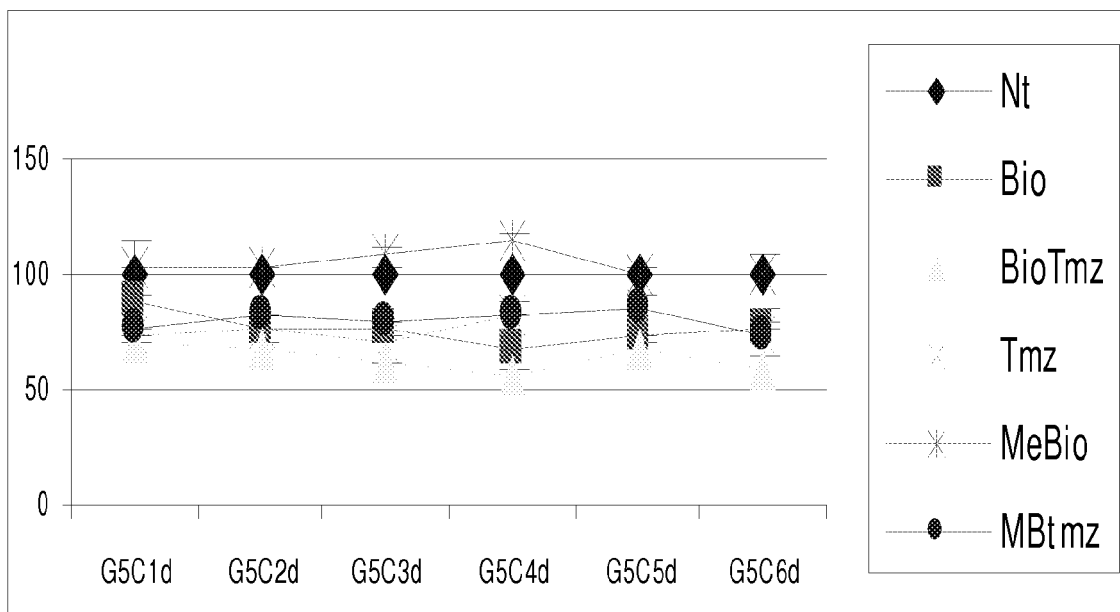
Figure 11:
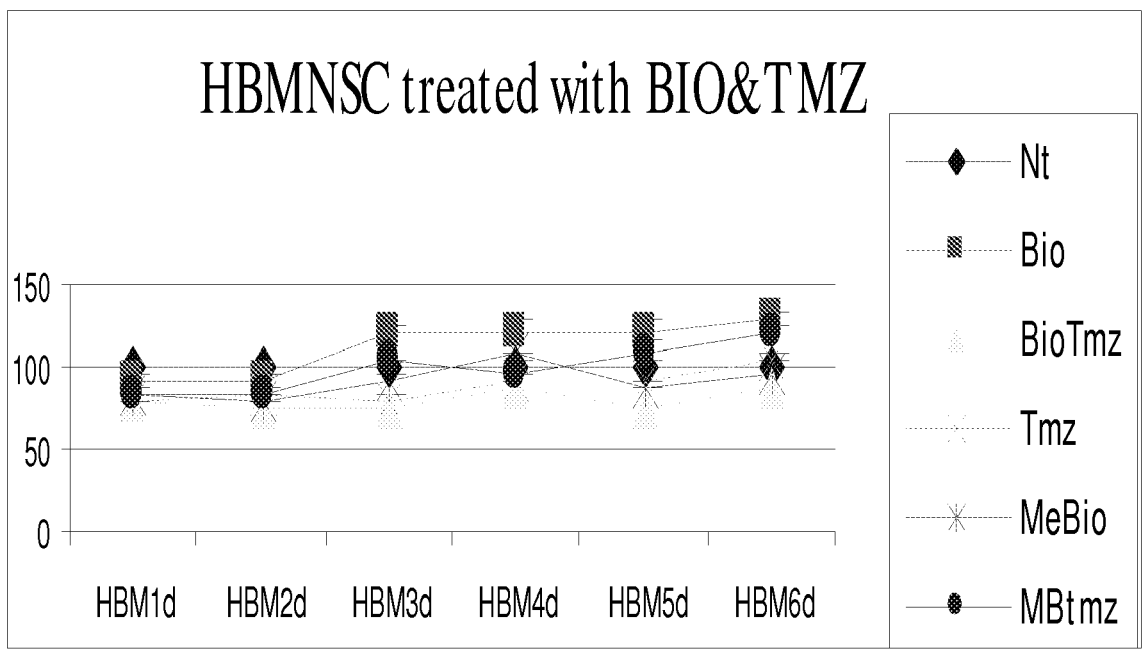
FIG. 11 depicts the time course of hBMNSC treated with BIO, BIO+Tmz, Tmz, MeBIO, MeBIO+Tmz, or no treatment in accordance with various embodiments of the present invention.
Figure 12:
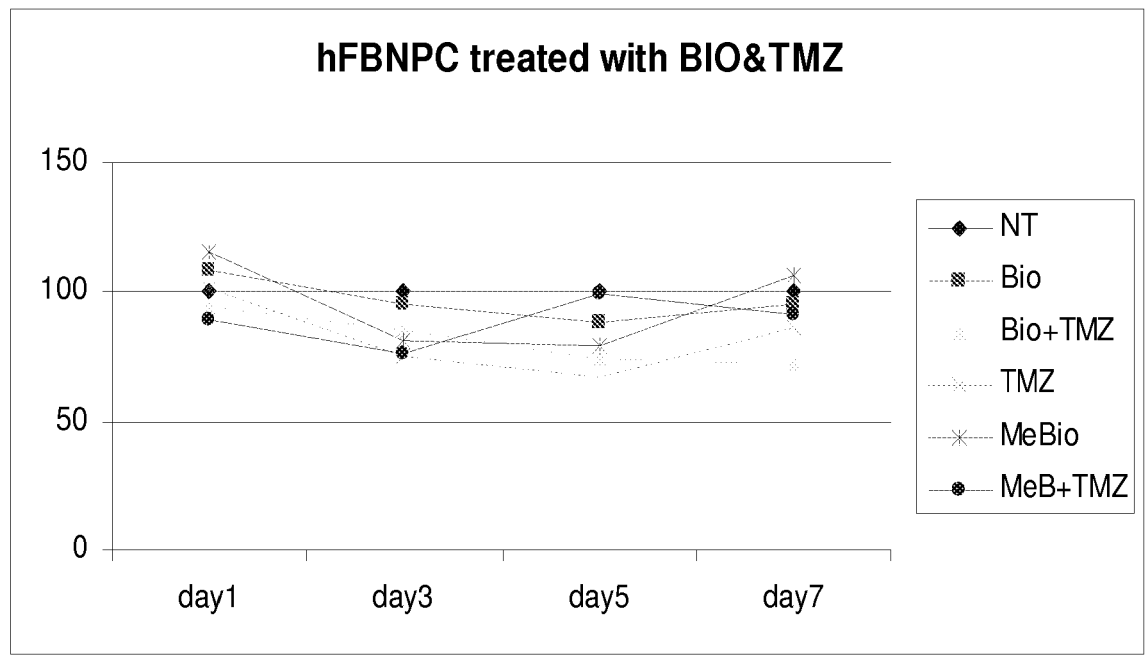
FIG. 12 depicts the time course of hFBNPC treated with BIO, BIO+Tmz, Tmz, MeBIO, MeBIO+Tmz, or no treatment over the course of seven days in accordance with various embodiments of the present invention.
Figure 13:
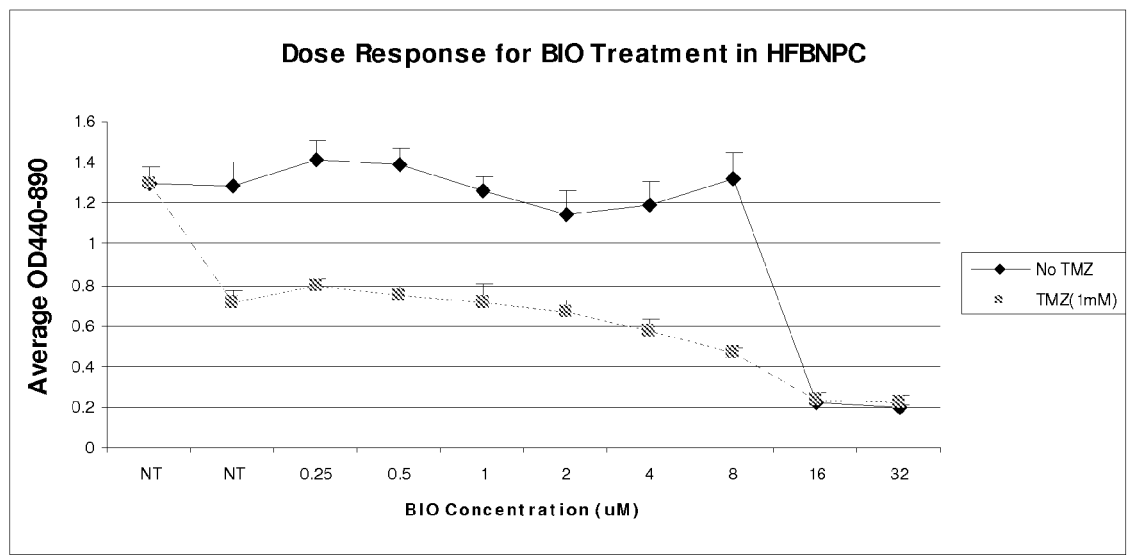
FIG. 13 depicts dose response for BIO and MeBIO treatment in HFBNPC in accordance with an embodiment of the present invention. (A) BIO Treatment; (B) MeBIO Treatment.
Figure 13:
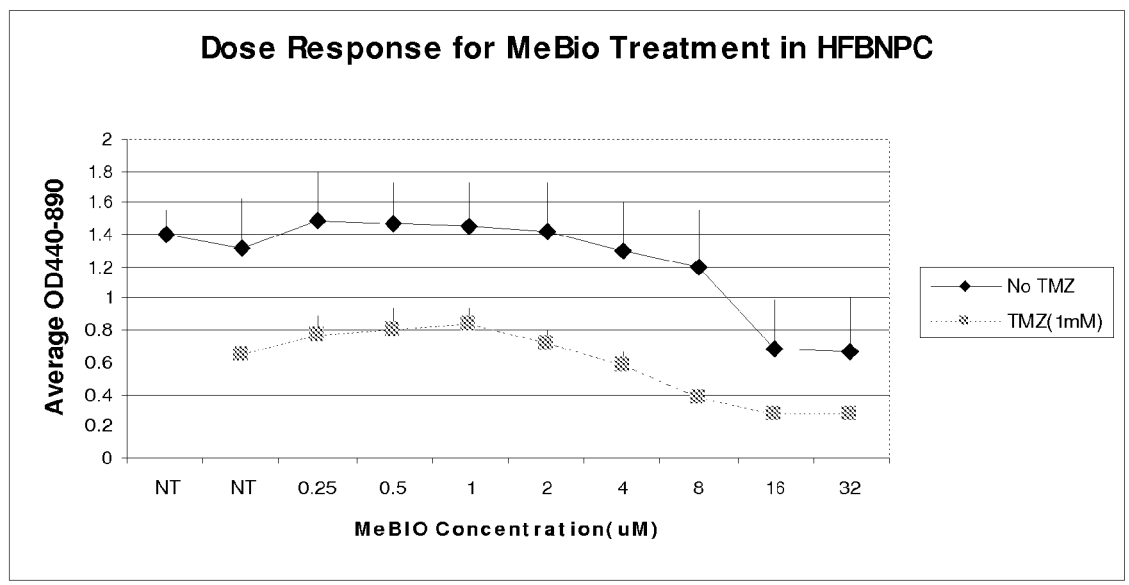

Apoptosis assays for BIO treated cells were performed. The results are summarized and depicted in table 2 and FIG. 4.

TABLE 2

|  | cells | U373 | LN18 | U87 | U343 | CSC | hBMC | Das | DA | CNSC | FBNSC |
|---|---|---|---|---|---|---|---|---|---|---|---|
| LR(apoptosis) | BIO− | 3.82 | 20.7 | 4.04 | 7.19 | 19.35 | 8.19 | 1.63 | 3.58 | 2.04 | 15.93 |
|  | BIO+ | 12.93 | 10.01 | 1.93 | 17.33 | 9.62 | 8.91 | 1.12 | 3.79 | 0.91 | 0.06 |
| UR(apop + nec) | BIO− | 4.13 | 3.8 | 3.16 | 2.8 | 3.84 | 1.41 | 0.69 | 0.9 | 60.64 | 48.12 |
|  | BIO+ | 8.33 | 2.38 | 2.24 | 9.49 | 2.71 | 1.26 | 0.89 | 0.9 | 48.05 | 15.5 |
| UL(necrosis) | BIO− | 1.44 | 0.24 | 3.17 | 7.42 | 0.17 | 0.32 | 1.12 | 2.07 | 13.13 | 10.28 |
|  | BIO+ | 0.73 | 0.45 | 2.36 | 4.9 | 0.26 | 0.44 | 1.34 | 2.55 | 37.16 | 63.24 |

Example 4

Cell Cycle Assay

Table 3 summarizes the data from the cell cycle assays.

TABLE 3

| | Cell Cycle (%) | | | |
|---|---|---|---|---|
| | G0-G1 | G2-M | S | G2/G1 |
| CSC1 − BIO | 79.28 | 2.73 | 17.99 | 2 |
| CSC1 + BIO | 66.49 | 8.26 | 25.24 | 2 |
| U343 − BIO | 50.78 | 23.06 | 26.16 | 1.71 |
| U343 + BIO | 42.74 | 10.57 | 46.68 | 1.85 |
| DA − BIO | 60.26 | 9.37 | 30.37 | 1.93 |
| DA + BIO | 66.21 | 8.07 | 25.72 | 1.94 |
| CSC2 − BIO | 55.8 | 2.64 | 41.56 | 1.99 |
| CSC2 + BIO | 65.89 | 7.25 | 26.86 | 1.88 |
| LN18 − BIO | 58.23 | 7.5 | 34.27 | 1.96 |
| LB18 + BIO | 59.54 | 9.5 | 30.97 | 1.95 |
| CSC3 − BIO | 70.22 | 10.61 | 19.16 | 1.92 |
| CSC3 + BIO | 74.44 | 7.83 | 17.73 | 1.91 |
| FBNSC − BIO | 65.06 | 4.64 | 30.31 | 1.96 |
| FBNSc + BIO | 71.84 | 8.43 | 19.73 | 1.88 |
| HBMC − BIO | 92.75 | 0 | 7.25 | 1.74 |
| HBMC + BIO2 | 91.08 | 0 | 8.92 | 2.08 |
| HBMC + BIO10 | 89.12 | 0.01 | 10.87 | 1.8 |
| U87 − BIO | 80.79 | 9.6 | 9.61 | 1.76 |
| U87 + BIO | 83.34 | 5.21 | 11.45 | 1.84 |
| DAs − BIO | 70.07 | 0.21 | 29.72 | 1.97 |
| DAs + BIO | 76.73 | 2.86 | 20.41 | 1.95 |

Example 5

Cell Groups

The following types of cells were used: (1) Cancer stem cells (CSC); (2) common cancer cells (adherent (Adh), paired to cancer stem cells); and (3) normal neural stem cells (e.g., normal human fetal brain derived neural progenitor cells (FBNPC); (4) brain tumor cell lines (e.g., U87, U343, U373, LN18).

Example 6

Treatment Groups

The follow treatment groups were used: (1) no treatment (NT); (2) BIO only; (3) Tmz only; (4) BIO+Tmz; (5) MeBIO (methylated BIO, analog of BIO) only; and (6) MeBIO+Tmz.

Example 7

Immunoassaying

Cells were stained for CD133 and nestin to clarify stem cells. Fluorescence-activated cell-sorting (FACS) was used to count the percentage of CD133+ cells.

Example 8

Gene Array Assay

Gene array assays were used to discover the role of signal pathway in different cells.

Example 9

RT-PCR

RT-PCR was used to confirm significantly different gene expression for different cells. RT-PCR for expression of different genes in cancer cells and hFBNPC are summarized in table 4.

TABLE 4

| | birc1 | birc3 | pparg | mmp7 | ccnd1 | tcf7 | mdm2 | pten | p53 | cMyc | birc5 | p21 | GSK3b | bCat |
|---|---|---|---|---|---|---|---|---|---|---|---|---|---|---|
| Ave t/c | 2.12 | 9.74 | 43.87 | 4.87 | 22.54 | 6.87 | 4.77 | 3.01 | 1.41 | 14.23 | 1.84 | 3.52 | 2.55 | 1.04 |
| Ave c/t | 0.97 | 0.36 | 0.25 | 16.05 | 0.20 | 0.51 | 0.34 | 0.46 | 1.03 | 0.85 | 0.86 | 0.48 | 0.58 | 1.15 |
| fb/CSC | 2.17 | 3.13 | 5.29 | 30.10 | e | 7.50 | 0.19 | 57.73 | 0.31 | 3.14 | 4.01 | 0.66 | 1.09 | 1.11 |
| CSC/fb | 0.49 | 0.21 | 0.02 | 0.03 | 0.00 | 0.14 | 6.06 | 0.02 | 3.64 | 0.37 | 0.25 | 1.51 | 1.13 | 0.93 |

Example 10

Western Blot

Western blotting was used to confirm gene expression.

Example 11

Change-Fold of Gene Expression in GBM CSC Compared to GBM Adherent Cells

Glioblastoma derived cancer stem cells (GBM CSC, spheres) were isolated from glioblastoma patients and their signal transduction gene expression patterns were compared to those of glioblastoma cancer cells (GBM Adh) from the same patients and also to those of normal human fetal brain derived neural progenitor cells (hFBNPC) using microarray. The results were confirmed by real-time PCR. The level of expression of genes related to cell proliferation pathways such as those found in the WNT signaling pathway and Hedgehog pathway were low in GBM CSC samples compared to GBM Adh. In contrast, genes related to NF-KB pathway such as birc1, birc3, NFKB1, survivin, MCP-1, MMP7 and VCAM were strongly up-regulated. On the contrary, NF-kappa B inhibitor, IKBKB was down-regulated in GBM Adh compared to GBM CSC. The genes in NF-kappa B pathway are known to be important for controlling cancer stem cell's apoptosis, survival, migration, and adhesion. In addition to those cells, the inventor found that gene expression pattern in GBM Adh was different from hFBNPC, especially for those genes related to p53 signal pathway (TN-FRSF6, 5.29 fold lower; TNFRSF10, 1.84 fold lower; MDM2, 4.74 fold higher). The results are summarized in table 5.

TABLE 5

Change-fold of Gene Expression in GBM CSC Compared to GBM Adherent Cells

| Pathway | Increased Expression of Genes | Decreased Expression of Genes |
|---|---|---|
| WNT | VEGF(1.75), WISP2(2.63), WISP3(2.19) | PPARG(5.19), TCF-7(5.59), CCND1(15.63), LEF1(1.46), MYC(1.25), Survivin (Birc5)(1.84) |
| Hedgehog | BMP2(1.30), FOXA2(1.32) | BMP4(1.35), EN1(1.60), PTCH(1.78) |
| NF-KB | BIRC1(1.86), NFKB1(1.32), NOS2A(2.51), MCP-1(2.08), MMP7(16.05), VCAM(1.93) | ICAM(1.42), IKBKB(1.58), |
| p53 pathway | GADD45(1.73) | MDM2(4.74), Fas(5.29), TNFRSF10(1.84) |
| PI3/AKT | MMP7(16.05), FN(2.13) | CCND1(15.63), BCL2(1.52), MYC(8.95) |

Example 12

Genotype and Expression Change-Fold by BIO Treatment

Genotype and expression change-fold by BIO treatment is summarized in table 6 and table 7. To compare the different signal pathway genes' expression in different cells, the inventor also utilized BIO, which has been identified as a GSK-3β inhibitor to activate the Wnt signaling pathway implicated in proliferation and maintenance of stem cells to further authenticate the importance of signaling pathway in the control of cancer stem cells. The results confirmed that the cancer stem cell's inactive genes may be aroused by BIO. Furthermore, the mechanism for regulation of gene activation by BIO not only related to WNT pathway but also to other pathways which are important in regulation and controlling of cell cycle, apoptosis and survival.

TABLE 6

| Fold to BIO− | Cells | U373 | LN18 | U87 | U343 | CSC | hBMC | Das | DA | CNC | FBNSC |
|---|---|---|---|---|---|---|---|---|---|---|---|
| p53 | | mutant | mutant | wild | wild | | | | | | |
| pten | | mutant | wild | mutant | mutant | | | | | | |
| Fold to BIO− | p53 | 0.71 | 0.93 | 0.66 | 1.41 | 0.38 | 0.62 | 1.07 | 0.44 | 0.66 | 0.47 |
| | pten | 2.3 | 1.15 | 2.83 | 3.48 | 0.81 | 4.29 | 4 | 0.44 | 1 | 0.54 |
| | MDM2 | 0.66 | 0.44 | 0.54 | 0.76 | 1.87 | 0.62 | 0.31 | 0.31 | 1.62 | 0.25 |
| | p21 | 0.34 | 1.32 | 1.04 | 0.84 | 0.62 | 1.23 | 0.48 | 0.97 | 1.68 | 0.28 |

TABLE 7

| | G1 CSC | G1 Adh | G7 CSC | G7 Adh | G10 CSC | G10 Adh | G17 CSC | G17 Adh | hFBNPC | hBMNSC |
|---|---|---|---|---|---|---|---|---|---|---|
| p21 | 6.7 | 7.2 | 7.5 | 5.6 | 6.5 | 4 | 9.5 | 6.2 | 19.3 | 5.2 |
| cMyc | 15 | 10.1 | 14.8 | 10 | 13.2 | 12.9 | 13.3 | 12.3 | ND | 15 |
| PDK1 | 8.2 | 8 | 9.8 | 8.7 | 8.3 | 7.4 | 6.9 | 8.1 | 2.9 | 9.8 |
| PKB | 6.6 | 6.2 | 10.7 | 7.7 | 6.7 | 6.5 | 12.1 | 10.4 | 0.7 | 7.3 |
| PI3K | 11.5 | 9.4 | 11.9 | 8.3 | 12.8 | 7.2 | 12.2 | 11.9 | 19.4 | 9.9 |
| CDK2 | 5.9 | 5.6 | 7.8 | 7.2 | 6.6 | 6.5 | 8.6 | 10.4 | ND | 9 |
| CCNE | 10.6 | 9.7 | 13.6 | 10.6 | 11 | 10.6 | 8.6 | 10.6 | ND | 11.9 |
| GAPDH | 0 | 0 | 0 | 0 | 0 | 0 | 0 | 0 | 0 | 0 |

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method to increase the cytotoxic effect of a chemotherapeutic drug in a subject in need thereof, comprising:
providing a glycogen synthase kinase-3 ("GSK-3") antagonist and/or Wnt canonical pathway agonist;
administering the GSK-3 antagonist and/or Wnt canonical pathway agonist to increase the cytotoxic effect of the chemotherapeutic drug; and
administering the chemotherapeutic drug to the subject.

2. The method of claim 1, wherein the GSK-3 antagonist and/or Wnt canonical pathway agonist is 6-bromoindirubin-3'-oxime ("BIO") or methylated BIO ("MeBIO").

3. The method of claim 2, wherein the GSK-3 antagonist and/or Wnt canonical pathway agonist is BIO.

4. The method of claim 2, wherein the GSK-3 antagonist and/or Wnt canonical pathway agonist is MeBIO.

5. The method of claim 1, wherein the chemotherapeutic drug is selected from the group consisting of temozolomide ("Tmz"), VP-16, paclitaxel, carboplatin, tumor necrosis factor-related apoptosis-inducing ligand ("TRAIL"), troglitazone ("TGZ"), pioglitazone ("PGZ"), rosiglitazone ("RGZ"), and ciglitazone ("CGZ"), procarbazine, vincristine, BCNU, CCNU, thalidomide, irinotecan, isotretinoin, imatinib, etoposide, cisplatin, daunorubicin, doxorubicin, methotrexate, mercaptopurine, fluorouracil, hydroxyurea, vinblastine, and combinations thereof.

6. The method of claim 5, wherein the chemotherapeutic drug is Tmz.

7. The method of claim 1, wherein the GSK-3 antagonist and/or Wnt canonical pathway agonist is 6-bromoindirubin-3'-oxime ("BIO") or methylated BIO ("MeBIO") and the chemotherapeutic drug is Tmz.

* * * * *